(12) United States Patent
DelMain

(10) Patent No.: US 6,774,157 B2
(45) Date of Patent: Aug. 10, 2004

(54) BIOCOMPATIBLE MEDICAL DEVICES WITH POLYURETHANE SURFACE

(75) Inventor: Gregory Jay DelMain, Valencia, CA (US)

(73) Assignee: Transoma Medical, Inc., Arden Hills, MN (US)

( * ) Notice: Subject to any disclaimer, the term of this patent is extended or adjusted under 35 U.S.C. 154(b) by 81 days.

(21) Appl. No.: 09/962,727

(22) Filed: Sep. 25, 2001

(65) Prior Publication Data

US 2002/0111393 A1 Aug. 15, 2002

Related U.S. Application Data

(62) Division of application No. 09/329,869, filed on Jun. 11, 1999, now Pat. No. 6,323,256, which is a continuation of application No. PCT/US97/23229, filed on Dec. 12, 1997.
(60) Provisional application No. 60/033,157, filed on Dec. 13, 1996.

(51) Int. Cl.⁷ .............................. B05D 3/04; C08F 6/00
(52) U.S. Cl. ...................... 523/112; 427/335; 528/493; 528/494; 604/96.01; 606/195
(58) Field of Search ................................ 523/105, 112; 427/335; 528/493–494; 604/96.01; 606/195

(56) References Cited

U.S. PATENT DOCUMENTS

| | | | |
|---|---|---|---|
| 3,663,288 A | 5/1972 | Miller | 117/7 |
| 3,807,054 A | 4/1974 | Joseph et al. | 34/73 |
| 4,302,418 A | 11/1981 | Cullis et al. | 264/341 |
| 4,371,686 A | * 2/1983 | Yamamoto et al. | 528/76 |
| 4,475,972 A | 10/1984 | Wong | 156/167 |
| 4,529,563 A | 7/1985 | McGinniss | 264/83 |
| 4,536,179 A | 8/1985 | Anderson et al. | 604/266 |
| 4,656,083 A | 4/1987 | Hoffman et al. | 428/265 |
| 4,713,402 A | 12/1987 | Solomon | 523/112 |
| 4,882,148 A | 11/1989 | Pinchuk | 424/423 |
| 4,896,671 A | * 1/1990 | Cunningham et al. | 600/374 |
| 4,990,357 A | 2/1991 | Karakelle et al. | 427/2 |
| 5,147,724 A | 9/1992 | Eschwey et al. | 428/409 |
| 5,415,636 A | * 5/1995 | Forman | 604/101.03 |
| 5,711,753 A | * 1/1998 | Pacella et al. | 600/16 |
| 6,033,582 A | * 3/2000 | Lee et al. | 216/37 |
| 6,120,847 A | 9/2000 | Yang et al. | 427/335 |

FOREIGN PATENT DOCUMENTS

| | | | |
|---|---|---|---|
| BE | 531794 | 3/1955 | |
| GB | 531794 | 1/1941 | |
| JP | 42-014315 | 11/1942 | |
| JP | 187506 | 9/1985 | ............ B27D/5/00 |
| WO | WO 83/00695 | * 3/1983 | |

* cited by examiner

*Primary Examiner*—Peter Szekely
(74) *Attorney, Agent, or Firm*—Schwegman, Lundberg, Woessner & Kluth, P.A.

(57) ABSTRACT

A system for improving the biocompatibility of medical devices present within a patient's body. In one embodiment, the present subject matter reduces the thrombogenicity of polyurethane materials in contact with the blood of a patient. In one embodiment, the medical device has a polymeric wall and a coating of polyurethane, said coating of polyurethane having the same chemical composition throughout the thickness and displaying an antithrombogenic effect when inserted into a patient's body in contact with blood for a period of at least twenty-four hours. The present subject matter relates to the manufacture and treatment of polymeric materials that may be inserted as medical devices, accessories, implants or replacements into animal bodies, such as the human body.

18 Claims, No Drawings

BIOCOMPATIBLE MEDICAL DEVICES WITH POLYURETHANE SURFACE

CROSS-REFERENCE TO RELATED APPLICATIONS

This application is a division of U.S. patent application Ser. No. 09/329,869, filed on Jun. 11, 1999, now U.S. Pat. No. 6,323,256, which is a continuation of International Patent Application No. PCT/US97/23229, filed on Dec. 12, 1997, which is an international filing of U.S. Provisional Patent Application No. 60/033,157, filed on Dec. 13, 1996, the specifications of which are incorporated herein by reference.

STATEMENT OF GOVERNMENT RIGHTS

Portions of this invention were developed under Grant No. 2 R44 HL55823-02 awarded by the U.S. Department of Health and Human Service. The U.S. Government may have certain rights in this invention.

BACKGROUND OF THE INVENTION

1. Field of the Invention

The present invention relates to the manufacture and treatment of articles and devices which may be temporarily, long-term, or permanently inserted as medical devices, accessories, implants or replacements into animal bodies, such as the human body. The present invention particularly relates to the manufacture and treatment of polymeric articles such as implants, prostheses, catheters, stents, shunts, heart valves and ducts for use in animal bodies.

2. Background of the Art

Modern medicine has enabled the use of many newer, non-classical surgical invasive techniques in the treatment of diseases. Implantation of temporary or permanent structural and functioning elements has become commonplace, while merely twenty years ago, such implants were quite rare. Early implants were limited to surgical grade metals and were primarily used for gross mechanical repairs such as bone securement or replacement Even today, oral surgery supports for permanent dentures are still made from surgical grade metal (e.g., titanium) as are Selby and Spinetech™ back surgery medical devices.

Improvements in the chemical types of and construction techniques for polymeric materials has enabled a broader use of these materials in the medical field. Typical areas where polymeric materials are used within the bodies of patients include, but are not limited to catheters, shunts, mesh closures or patches (e.g., vascular grafts), general prostheses construction, artificial muscle attachments (e.g., artificial ligaments), insulation for electrical devices (e.g., for pacemakers and drug delivery systems), and the like. Many early attempts at the use of polymeric materials within patients resulted in rejection, physical irritation, rapid deterioration of the composition, cracking and fissuring, and thrombus formation. The formation of blood clots is particularly dangerous where the inserted object has a lumen which can be closed or restricted by the clot, either blocking the function of he tube or being sloughed off, causing a phlebitic, stroke-like, or other non-conductive event within the patient.

U.S. Pat. No. 4,475,972 describes the formation of prostheses, by the extrusion or spinning of polymer fibers into porous vascular grafts. The fine nature of the fibers used in the grafts has been identified as a possible source of thrombogenic activity when fibers break or crack.

U.S. Pat. No. 4,882,148 describes implantable polymeric devices with reduced cracking and thrombogenic problems by treating the surfaces of the polymeric implantable material with a sulfonating agent, such as sulfur trioxide and fuming sulfuric acid. The sulfur trioxide may also be provided in combination with a primary alcohol. Treatment may be effected by dipping in the sulfonating composition or, in the case of sulfur trioxide, by directly exposing the prostheses to sulfur trioxide vapor. This reference indicates that a chemical reaction occurs between the sulfonating agent and the filaments, because it is specifically indicated that the porous networks generally cannot withstand the heat of reaction from these concentrated sulfonating agents which tend to melt or distort the porous network before the sulfonation reaction is complete. The fact that sulfonation of the polymer can be observed after neutralization treatment indicates a chemical reaction which attaches sulfur containing moieties into the polymer composition of the implant.

U.S. Pat. No. 4,713,402 describes the use of solutions of particular ratios of chlorofluorocarbon compounds and petroleum ether, and after exposure of the devices to the solutions, the treated device is exposed to the application of antithrombogenic/antibacterial agents. The patent also provides a good background description of prior art techniques for heparinizing polymer surfaces to reduce blood-polymer interactions.

U.S. Pat. No. 4,656,083 describes the use of non-chemical means (gas plasma discharge) to improve the biocompatability of biomaterials.

U.S. Pat. No. 4,536,179 describes the application of thin films of plasma polymerized fluorocarbon coatings on the surface of catheters to improve their long term bio-acceptability.

U.S. Pat. No. 5,147,724 describes the use of a gas mixture comprising fluorine and a gaseous oxidizing agent to improve the smoothness of plastic surfaces such as polymers of ethylene, propylene, butadiene, polystyrene and hydrocarbon compounds.

U.S. Pat. No. 4,529,563 describes the treatment of thermoplastic surfaces with a vapor phase of solvents which form an azeoptropic mixture. The solvents comprise both a 'destructive' solvent and a 'non-destructive' solvent. The treatment is said to improve the physical properties of the thermoplastic substrate.

U.S. Pat. No. 4,302,418 describes a fluid medium used in a process for polishing surfaces of plastic components which is insoluble or inert within the fluid medium until an elevated temperature is reached. It is described as particularly useful for polishing the internal surfaces of tubing components for medical equipment The process includes applying a vaporized solvent at an elevated temperature to liquefy or melt insoluble plastic component surfaces without deforming the component, followed by solidifying or freezing the surfaces by removing the component from the vapors.

U.S. Pat. No. 3,807,054 describes a process for enhancing the appearance of plastic articles such as telephone cases comprising treating the plastic articles within a gas-tight environment with a vapor at an elevated temperature to liquefy the surface of the plastic and then cooling the plastic to return the surface to a solid state. This removes large scratches from the surface of relatively thick articles such as telephone casings.

SUMMARY OF THE INVENTION

The present invention provides a method for improving the bio-compatibility of medical devices which are invasively present within a patient's body. The present invention particularly reduces the thrombogenicity of polyurethane materials in contact with the blood of a living patient. The method comprises providing a bio-compatible medical device having polymeric polyurethane components thereon, exposing the polyurethane components of the medical device to polar solvents for said polymeric components while the polar solvents are in the vapor phase (i.e., without direct physical contact of the polymeric component to a mass of liquid solvent, although some condensation may occur on the surface of the polyurethane), and allowing said vapor phase exposure to continue for a sufficient amount of time as to soften at least some irregular or sharp features on the surface of the polymeric component.

The invention describes a method of improving a medical device having at least one polymeric component, the process comprising the steps of providing a vapor phase comprising a solvent for said polymer component, and exposing said polymeric component to said vapor phase. The process comprises taking a polyurethane component has a surface with a topography (e.g., roughness, sharp edge features, deviations from planarity and the like), and exposing the polyurethane component to said vapor phase increases planarity in said topography. This is done without altering the chemical compositiomn of the polymer component or without necessarily effecting a chemical reaction between the solvent and the polymer component, and because of the control of the amount of solvent which can contact the polymer, the potential for damage to the polymeric component is reduced. In particular, the vapor phase treatment will reduce the dimensions of extrusion markings on the exterior surface of the polyurethane with minimum potential for damage to the structure of the polyurethane, even where the polyurethane is present as thin walls (e.g., less than 0.0762 mm).

Polyurethane articles having wall thicknesses of less than about 3 mils (e.g., less than about 0.076 mm) can be treated with this process to reduce surface roughness without damaging the structural integrity of the article. In this way, thin walled catheters, with wall thicknesses of 0.076 mm and less can be treated to reduce surface roughness without causing structural damage to the catheter. The catheters themselves are novel in being non-thrombogenic and having thin walls (herein defined as having walls equal to or thinner than about 0.076 mm).

DETAILED DESCRIPTION OF THE INVENTION

Polymeric compositions which are generally useful in the medical device industry for implantation include, but are not limited to polyurethanes, polyolefins (e.g., polyethylene and polypropylene), poly(meth)acrylates, polyesters (e.g., polyethyleneterephthalate), polyamides, polyvinyl resins, silicon resins (e.g., silicone rubbers and polysiloxanes), polycarbonates, polyfluorocarbon resins, synthetic resins, and polystyrene. These materials, whether directly extruded, molded, or formed from extruded fibers, but particularly where formed by an extrusion process, tend to have irregular surface features, such as pits, bumps, rough elevations, and other topographic features which deviate from planarity and smoothness. Grooves or rows of material are particularly noticeable when the polyurethane has been extruded. It is these very non-planar features which can act as thrombogenic sites on the polymeric surfaces. Prior art techniques of applying coatings to the surfaces (e.g., U.S. Pat. No. 3,663, 288) can mask some of these defects, but they may also cause problems if the coatings are not uniform or if the coating solvents damage the underlying structure or alter its physical properties. By applying a coating, two layers must be controlled and be compatible rather than just a single layer of material.

The present invention provides a method for at least reducing surface irregularities or non-planarities in a polyurethane surface of a medical component by exposing the polymeric component to a vapor phase which contains at least one solvent which is capable of swelling, softening and/or dissolving the polymeric component. The exposing is carried out without direct contact of the polymeric component with a significant volume of liquid solvent, even though some condensation may occur from the solvent vapor onto the surface of the polyurethane component The amount of time during which the polymeric component is exposed to the vapor phase of the solvent is selected so that at least some non-planar feature of the surface is reduced in size or magnitude. For example, if the angularity of a raised sharp feature is reduced, if small fibrils are fused more strongly to the mass of the polymeric component, if sharp features around holes or lumens are smoothed, if small fissures are closed, or if any other such beneficial modification of the topography is effected by the exposure to the vapor phase of solvent, then benefits have been contributed by the practice of the invention. Depending upon the vapor concentration, the solvent activity of the [particular solvent to the polymer, and the degree of modification needed or desired, exposure may be for seconds to minutes or more. For example, in a 100% solvent vapor environment with a very strong solvent for a particular polymer component on the device, an exposure for one second may be sufficient Providing a heated vapor environment can assist in reducing or minimizing the exposure time without adversely affecting the results. Lower vapor concentrations may be desirable with extremely fine polymer component elements, so as to provide greater time latitude in the process, and in this manner the exposure time may be greatly extended up to many minutes (e.g., sixty minutes).

The process of the present invention may be summary as a process of improving a medical device having a polyurethane component, the process comprising the steps of providing a vapor phase comprising a polar solvent for said polyurethane component, and exposing the polyurethane component to the vapor phase. This activity reduces the dimensions of wave patterns, wave events, or disuniformities in the surface, usually caused by streaking during extrusion of the catheter. The polyurethane component before treatment has a surface with a topography, and exposing the polyurethane component to the polar vapor phase increases planarity in the topography. It is preferred that the solvent is at least as polar as toluene, and that temperatures be used which do not alone or in combination with the solvent destroy the polymer integrity. This temperature is above the boiling point of the solvent, but usually below 120° C. In one preferred embodiment, the vapor phase comprises a solvent consisting essentially of two different solvents, preferably two different organic solvents. The vapor phase is usually at a temperature above 40° C., and the preferred vapor phase comprises tetrahydrofuran (THF) and dioxane. The process results in a medical device for insertion into an animal body, the device comprising at least one element having a wall of polyurethane which is about 0.076 mm or less in thickness, the wall of polyurethane displaying no thrombogenic effect when inserted into an animal body in contact with blood for a period of at least twenty-four hours. A thrombogenic effect may be determined by many different techniques, some of which are reviewed elsewhere herein. The absence of a thrombogenic effect of course means any significant thrombogenic effect. For example, pressure drop through the catheter would be an indication of possible thrombogenic activity, but other contemporaneous events could also influence the blood pressure or pulse pressure drop measured through the catheter. Therefore only significant effects within the tolerance of the system for measuring the pressure and indicating some significant effect are to be of any concern. For example, if there were a measured drop of 5 mm of mercury in the difference between systolic and diastolic pressure measured through the catheter in the first three hours, but over the course of the next twenty four hours there were no more significant drops, the activity causing the reduced pressure would not likely be any thrombogenic activity. If it had been thrombogenic in nature, the degree of pressure drop would have assuredly continued to increase over the initial results.

Preferred medical devices comprise a catheter, stent or shunt for insertion into an animal body, the device comprising at least one wall of polyurethane which is about 0.076 mm or less in thickness, the wall of polyurethane displaying no significant thrombogenic properties or having no significant thrombogenic effect when inserted into an animal body (including humans) in contact with blood for a period of at least twenty-four hours. A specific preferred medical device is a infusion catheter, and the process can be performed without damage to the porosity of the openings effecting infusion through the catheter. The medical device may be a catheter having an outside dimension of 1.5 mm or less and a wall thickness of about 0.076 mm or less, for example, a catheter having an outside dimension of 1.0 mm or less and a wall thickness of about 0.076 mm or less, or a catheter having an outside dimension of 0.5 mm or less and a wall thickness of about 0.05 mm or less. The device may be a catheter having an outside dimension of 1.0 mm or less and a wall thickness of about 0.076 mm or less, and the outer surface of said catheter has on average no more than one topographic wave event per 100 square micrometers with the distance from the maximum height of peaks to the maximum depth of an adjacent valley of more than 0.1 micrometers. Another medical device comprises a tubular catheter, stent or shunt for insertion into an animal body, said device comprising at least one wall with an outer surface of polyurethane, which wall is about 0.076 mm or less in thickness, said device having an outside diameter of 1.0 mm or less and a wall thickness of about 0.076 mm or less, and wherein the outer surface of said catheter has on average no more than one topographic wave event per 100 square micrometers with the distance from the maximum height of peaks to the maximum depth of an adjacent valley of more than 0.1 micrometers in the wave event The medical device preferably has on average no more than one topographic wave event per 100 square micrometers with the distance from the maximum height of peaks to the maximum depth of an adjacent valley of more than 0.05 micrometers in the wave event.

The surface characteristics of the extruded polyurethane catheter have been described as a "wave event" based upon scanning electron microscope images taken of the surfaces of the catheters at various magnifications, usually at about 1100×. The surface appears to have sinusoidal or rolling waves of structure, at least in part due to extrusion and cooling/solidifying effects on the catheter during manufacture. The wave events are dependent upon the extrusion process, but in the photographs available from the catheters used in the examples of the present invention with about 0.05 mm wall thickness, the waves were present in a frequency of about 4–10 waves per 10 linear micrometers, in cross-section to the waves. The height of the waves were difficult to measure, but appear to be at least about 0.4 or 0.5 micrometers from the height of the peaks to the depth of an adjacent valley. When dip treated in solvents or solutions, there is a definite reduction in the intensity of the amplitude of the wave pattern in thicker wall catheters (e.g., greater than 3 mils [greater than 0.077 mm]), but there is still clearly evident wave patterns and events on the surface. The amplitude of the events appears to have been diminished to about 0.15 or 0.2 micrometers in difference between peaks and adjacent valleys, but these effects with dipping have not been effective on thin wall catheters (e.g., equal to or below 0.076 mm) without significant structural damage to the catheter. In the practice of the present invention, the wave patterns within an average 100 square micrometer area have appeared to have been reduced to less than one event per area having an amplitude (between peak and adjacent valley) of 0.15 micrometers. In most instances, there appear to be fewer than one event per 100 square micrometers with amplitudes of 0.1 micrometers, 0.075 micrometers or even 0.05 or 0.025 micrometers. In some SEM images, there are no visible wave events in the photograph. Some incidental detritus may be present on some of the images, but there may be no visible wave events at 1100× magnification.

The prior commercial methods of smoothing polyurethane surfaces on catheters has comprised the dipping of the catheter into liquid solvent This treatment was acceptable for many medical devices, but was not useful in treating devices with thin walls or thin layers of polyurethane. In particular, when polyurethane layers or walls of less than 3 mils (0.0762 mm) were treated by dipping, the structure of the article, especially where used on thin walls of catheters, would not be satisfactory. Lack of satisfaction with the surfaces could range from complete collapse of the structure, warping or bending of the structure, disuniformity in the surface, and disuniformity in the edge of the surface. Even the best of results provided by the dipping of thin wall polyurethane catheters into polar solvents were predominantly less than desirable for other than short term (e.g., less than 3 hours) use of the catheter product with catheter walls of 2 mils (0.054 mm) or less, no clearly useful products were provided by dipping processes.

Visual observation of extruded thin wall catheters, dipped thin wall catheters (when they survived the process), and vapor treated thin wall catheters were clearly distinguishable. The extrusion process leaves grooves in the surface of the extruded polyurethane from imperfections in the die head or buildup on the extrusion head. These grooves are quite noticeable on the surface of the polyurethane. Their dimensions appear to be on the order of about 0.5 up to 1 micrometers before treatment. Dip treatment appears to reduce the size of the grooves (as measured from the height of a peak to the depth of an adjacent valley) usually to between about 0.3 to 0.7 micrometers, again noting that the dipping treatment is effective upon only thick walled catheters and can not be used to provide consistent results in thin wall catheters. Vapor treatment, even with the same solvents, in addition to being more gentle on the structural integrity of the article, has been found to reduce the groove dimensions (again as measured from the height of peak to the depth of an adjacent valley) to less than 0.3 or 0.2 micrometers, usually less than 0.15 micrometers, even less than 0.1 micrometers to a level where it is not even visible under SEM photographs at 1100×, which indicates that they are less than about 0.05 micrometers. These grooves are not merely occasional events on the surface of the extruded product, but rather are repeating structures on the surface with wave after wave of these peaks and valleys without interruption. These surface features are believed to directly contribute to thrombogenicity from the catheters. This can be seen in the fact that thin wall catheters of the present invention can have extended use within a patient of at least 3 days, usually at least 7 days, consistently above 14 days, and even for more than 30 days without any evidence of significant thrombogenicity in a living animal while the catheter is in contact with the blood stream in an aorta. Catheters with polyurethane surfaces which have been made by other processes may display thrombogenic behavior within hours or within one day of insertion into the aorta of a live animal.

Thrombogenic behavior can be identified by a number of events. The most dramatic evidence is paralysis of the patient, which is an insufficient event for purposes of enabling prevention of damage to a patient Another way of identifying thrombogenic behavior is by measuring the differential between the systolic and diastolic pressure (hereinafter referred to as the pulse pressure difference). The pulse pressure difference will drop by at least about 10 mm Hg when thrombosis begins to clog the fluid flow path of the catheter. The clogging may occur within the central area of the catheter or at the opening thereof. Other vents may affect the pulse pressure which are events independent of catheterization. For example, certain drugs, independent medical events (infarctions, stress, etc.), certain foods, allergies, and the like may affect blood pressure. However, to the degree that these other events are not direct effects upon blood pressure, a non-thrombogenic catheter according to the present invention is one which will not encounter a 10 mm Hg drop in pulse pressure difference within three hours or twenty-four hours, or 7 days, or 14 days or 30 days of insertion of a catheter into the aorta of a living mammalian patient. The assurance necessary for identification of the pressure drop being a result of thrombosis on the catheter can be assured by insertion of a new catheter into the same region of the aorta to determine if the measured pressure drop is an actual event within the patient or is in fact the result of thrombosis on the catheter.

Where the term "planarity" is used in describing effects on the polymeric component, the term refers to microscopic effects and not to macroscopic effects. For example, portions of the polymeric component may have originally been square or rectangular in crossection, and the solvent treatment smooths the corners into a more arcuate, curved shape which could be less irritating to a patient. Even though the macroscopic planarity may be altering the material from four planar faces to more curved features, the use of the term is not contradictory to planarity. The main effect is to remove features or reduce features which could irritate a patient The solvents selected are not independent variables in the practice of the present invention, but must be selected on the basis of their solvent activity with the particular polymeric materials used in the medical devices. There will even be some degree of variation in effects amongst different polyurethanes. The relationship of specific solvents with particular polymers is well understood in the art and the selection can be readily made by an ordinarily skilled polymer chemist. Solvents may be generally selected from amongst many polar organic solvents, for example, well known solvents such as alcohols, ethers, esters, amides, ketones, heterocyclic compounds, polar aromatic compounds, and mixtures thereof, even with compatible non-polar solvents. The solvents may also contain non-solvent ingredients which are carried into the vapor phase with the solvents, such as antibiotics, antifungal agents, antistatic agents, and the like. The vapor phase may comprise, consist essentially of, or consist of at least one solvent or multiple solvents for the polymeric components. As is recognized in the art, the individual solvent components may evaporate from the source of the vapor phase at different rates, altering the source composition and ultimately the vapor phase composition. To guard against this effect, the source of the vapor phase will often have to be replenished with a composition with different ratios of ingredients than the original source material and/or the vapor phase.

Preparation of the surface of materials used in medical implants and catheters used in humans and animals is often needed to improve biocompatibility and blood compatibility. Traditionally, this has been accomplished by a number of means. The most common means is application of a coating to the surface via a dipping process. This involves preparation of a solution of the material to be applied to the catheter surface dispersed in a solvent. The implant or catheter is then dipped in the solution. Following evaporation of the solvent off of the implant or catheter, the desired coating remains on the dipped surface. The disadvantages of this approach is that the resulting coating may be too thick for some applications, the dip coating may be uneven due to running of the solution when the catheter is removed from the dip solution, small holes or catheter lumens can be plugged with coating material, and the dip coating process can be labor intensive. In addition, if the solvent is too aggressive, it may not be possible to treat thin materials without causing distortion or damage. Another conventional means of surface preparation for catheters and implants is application of a coating on the surface of the implant or catheter via plasma deposition. This involves exposing the implant or catheter to a plasma created by a radio-frequency field in a near vacuum into which low concentrations of one or more gases are introduced. Gases are energized by the plasma resulting in a chemical reaction that causes the chemical nature of the surface of the implant or catheter to be modified or results in deposition of a thin layer of a coating that provides the desired surface properties. Disadvantages of this process include the fact that, depending upon the application of the device, it may be necessary for the surface of the implant or catheter to be relatively smooth prior to application of the coating, since this process is not capable of filling large voids or fissures in the material surface. In addition, the equipment needed for plasma deposition is quite expensive.

The present invention may also be used in preparing surfaces for application of other layers, rendering the prepared surface much smoother so that thinner over coated layers may be applied with greater uniformity in those coated layers and their surfaces. For example, if an anitbacterial silver layer were to be deposited on a polymer surface (not even necessarily a polyurethane surface, but some other polymer which may be smoothed by vapor phase treatment with an appropriate solvent, either polar or non-polar depending on the solvent/polymer relationship), less silver would have to be applied to get a smooth coating since the coating would have to mask fewer or smaller defects.

This invention provides a new and unique means of overcoming the limitations noted above. This means involves choosing a material for the implant or catheter: 1) that has a suitable chemical composition, that is a polyurethane, such that if the surface were highly finished (smooth), it would provide the desired properties of biocompatibility and blood compatibility (e.g., antithrombogenic) and; 2) that the polyurethane polymer is soluble in a polar solvent. Surface preparation is accomplished by exposing the solvent system to the catheter or implant to be treated in vapor form. It is preferred that the atmosphere be inert (e.g., inert gases such as nitrogen or the noble gases may provide a partial vapor phase background for the solvent system) and free of particles during exposure of the material to the vapor solvent system. Exposure of the material to the vapors causes dissolution and reflow of the surface of the material as well as rounding of corners or larger surface irregularities. The resulting surface can be extremely smooth, greatly increasing the biocompatibility and blood compatibility of the material. This process has been shown to be amendable to volume production, improved consistency, and greatly increased yields as compared to conventional techniques for surface preparation, particularly when the surface of the material has irregularities that often result from extrusion, molding, or forming. For a given material, the degree to which corners are rounded and the surface of the material is reflowed can be controlled by varying the amount of solvent added, the time of the exposure, and the temperature of the atmosphere. This process may also be useful for reducing the thickness (etching) the materials.

The process could be modified in a number of ways including, bringing the vapor concentration up and down in a predefined pattern so the solvent permeates the entire structure in an even fashion. Also, a specific temperature or pressure profile could be applied to effect overall, even attack by the solvent or to induce rapid effects on smaller structures with little effect on the bulk of the material. The technique could be hybridized with a dipping process in a number of ways. These include: using the vapor process to pre- or post-treat a dipped product, dipping the product under a vapor atmosphere to control uneven drying, or using a the solution in the form of finely divided particles (a fog or droplets) which could be deposited with or without the help of electrostatic precipitation.

An infusion catheter will be used in this example of the practice of the present invention. An infusion catheter is a catheter of approximately 3 feet (0.91 m) in length which is heat sealed at the distal end. Within the last one inch of that distal end are drilled 36 holes transverse to the axis of the catheter in a roughly equidistant manner. The drilled holes are approximately 0.010" (0.25 mm) in diameter. The catheter itself is made from and ether base polyurethane having an outer diameter of 0.030"(0.76 mm) and inner diameter of 0.016" (0.40 mm).

The procedure for washing the catheter prior to the vapor treatment has been omitted and is not necessary to obtain the desired effect but removes contaminants which would be impossible to remove after treatment.

The basic reaction vessel is a tall 300 ml Pyrex beaker. The solvent was placed into that beaker. A cover was fashioned to be placed at the top of the beaker to reduce the open area through which the solvent would escape into the atmosphere and be lost. Evaporation needs to be controlled because evaporation causes the specific ratio of the solvent to change, which results in a reduced or inconsistent effectiveness of the process.

The 300 ml beaker was held in place using a band clamp affixed to a standard chemistry support stand. A thermometer was also supported by a second clamp and was placed to measure the temperature of the vapors in the 300 ml beaker. The 300 ml beaker was placed inside of a second Pyrex beaker which had a 400 ml capacity. Approximately 50 ml of Dow Corning 200 (polydimethylsiloxane) fluid was placed in the second beaker to transfer heat to the first (300 ml) beaker. The second beaker was located on a hot plate with stirring capability. A stir bar was placed in the Dow 200 fluid. The hot plate was plugged into a temperature controller with the thermocouple from the controller being placed in the Dow 200 fluid. It is generally effective to set the temperature controller to 10 degrees C. higher than that desired for the vapors. The second beaker is wrapped over 90% of its circumference with a blanketing material to produce even heating. The remaining 10% of the circumference allows visual monitoring of the procedure.

When the proper temperature was reached, a reflux ring could be seen in the reaction (300 ml) beaker just above the level of the Dow 200 fluid in the second beaker. If boiling is evident in the reaction (300 ml) beaker, the temperature is too high or the solvent is too rich in THF.

If during processing the reflux ring disappears and the vapor temperature is at or above the recommended temperature, the operator should add THF slowly in 25 ml increments at 5 minute intervals until the ring reappears.

EXAMPLE 1

Treatment of a Infusion Catheter.

This procedure describes the process of treating the infusion catheters after the above described cleaning. The catheter is delicate and it is desirable to avoid scratches and abrasion or accumulation of dirt and other foreign particles. It is especially important to be careful in the region where the transverse holes are drilled. Clean room sleeves and sterile gloves were worn at all times during this procedure.

The catheter was grasped at the infusion end near the loop. The timer was set for an appropriate time, such as 15 seconds. The solvent temperature was 70 degrees C. plus or minus 1 degree C. The infusion end of the catheter ws lowered into the solvent container through the one inch center hole of the beaker cover to ¼ to ½ inch above the solution level, starting the timer simultaneously with the lowering of the catheter. When the timer expired, the catheter was withdrawn and placed on a nitrogen manifold to allow for vapor evaporation. Caution was taken to assure that the treated portion of the catheter did not come into contact with any solid or liquid materials for one hour after treatment After a minimum of one hour of nitrogen flow through the catheter in the manifold, the catheter was removed from the manifold, also removing the applicator tip from the catheter.

Second Catheter Vapor Treating Process

The procedure for treating a thermoplastic catheter was as follows. A clean catheter free of dirt and oils was treated by this procedure in a clean environment where airborne dust and debris have been greatly eliminated from the air. Failure to do so results in airborne particles becoming trapped on the surface of the treated product The cleaned catheter is introduced into a solvent vapor atmosphere to a sufficient depth to treat the desired length of the catheter. This usually means introducing the catheter into the beaker until the tip is 1 to 1.5 cm above the surface of the liquid phase of the solvent. The beaker is approximately 300 mm tall and the solvent depth is typically maintained at 5 mm. These conditions will allow the necessary 1 to 2 cm region at the tip of the catheter to be treated. Treatment of the balance of the catheter is not usually necessary because that portion is not exposed to blood flow, however, there is no evidence that treatment of those areas cause undesirable results. The beaker is of a double jacket design where a heated clear liquid (Dow 200 fluid) is allowed to flow in to and out of the volume between the walls. This provides for a convenient means to maintain the temperature within the beaker yet maintaining a clear view of the catheter during treatment. By adjusting the temperature of the heated liquid to a specified level below the boiling point of the solvent, the concentration of the vapors can be adjusted as can their aggressiveness on the catheter to be treated.

By varying the temperature and exposure time different results can be achieved. It has been noted that lower temperatures and longer exposure times result in small structure surface modification only while higher temperatures even with short exposure times of only tens of seconds will cause visible changes to the profile of the catheter such as a more rounded tip region. If the temperature is raised further the catheter will be destroyed in a only a few seconds. Exposure times and temperatures are specific to the solvent being used. It has been demonstrated that some solvents have no effect independent of the applied heat, while it is suspect that some are too aggressive to provide good control. Testing has shown that on a 16 mil catheter having a 2 mil wall thickness a two part solvent consisting of tetrahydrofuran and dioxane in a ratio of 3:1 at 65 degrees Celsius will consistently result in high quality catheters if left in the vapor bath for 25 seconds. To reduce the activity at the tip, nitrogen gas may be blown through the catheter at a rate of a few cubic centimeters per minute during the last 10 seconds of the treatment period. Varying results are to be expected as the dimensions of the catheter are varied. Larger heavy walled catheters benefit from longer exposure times. It is important that the catheter be exposed to vapors prior to annealing or other treatment steps as these processes can relieve internal stresses which are beneficial to the vapor process. The internal stress at the tip of the untreated catheter causes the tip to become rounded during vapor treating probably due to the urethane reflowing to seek a condition of lower stress. Once the process is completed, the material can be annealed if necessary and is ready for other processing. In some coating processes, it may be highly desirable to have the surface very smooth prior to application.

After treatmeant, the catheter surface is tacky and must be maintained in a similarly clean environment in which they were treated until the solvent has evaporated from the bulk of the catheter material. One specific advantage of the vapor treatment is this evaporation occurs more quickly than for catheters dipped in the solution of solids and solvent previously used for catheter treatment. This allows for more throughput in the treatment area.

EXAMPLES 3–13

Thin wall (0.2 to 0.3 mils, 0.05 to 0.076 mm) polyurethane extruded catheters were used in the following examples to evaluate the types of solvents and the various temperature conditions which could be used in the practice of the present invention.

| | |
|---|---|
| Solvent 1: | Dichloromethane. |
| Catheter 1: | Exposed to 30 degree C. vapors for 62 second without nitrogen flow and 28 seconds with nitrogen flow without any effects shown. |
| Catheter 2: | The temperature was raised to 35 degrees C. and the treatment time was 25 seconds (15 without nitrogen, 10 with). No effects were shown. |
| Catheter 3: | At 40 degrees C. the catheter began to lose stiffness and some streaking was apparent from solvent action. The time used is the same as for catheter 2. |
| Catheter 4: | Again using the same treatment duration as for catheters 2 and 3 the temperature was raise to 45 degrees C. The catheter tip collapsed and the material became very limp. |
| Conclusion: | Dichloromethane shows little promise for use in treating this urethane catheter material as a one component solvent vapor. |
| Solvent 2; | Acetone. |
| Catheter 1: | This and all acetone tests were conducted with a 25 second treatment period comprised of 15 seconds of exposure to the vapors with no nitrogen flow through the catheter and 10 seconds of exposure with a low rate of nitrogen flow through the catheter. This test was conducted at 41 degrees C. and no effect was noted. During this acetone test only, an additional 65 seconds of exposure (47 seconds without nitrogen flow, 18 seconds with) was allowed. Still no effect was noted on the condition of the catheter. |
| Catheter 2: | Raising the vapor temperature to 46 degrees C. resulted in a glossier appearance but no rounding of hard edges was noted. |
| Catheter 3: | No additional effects were noted in this catheter treated at 51 degrees C. |

-continued

| | |
|---|---|
| Catheter 4: | When the temperature was raised to 56 degrees C. some smoothing became apparent but insufficient to be considered suitable for implant. |
| Conclusion: | Acetone is a possibility for a one component or multiple component solvent for vapor treating at higher temperatures. Further investigation is warranted as this solvent is generally considered less toxic others considered to be highly effective in this process. |
| Solvent 3: | Hexane |
| Catheter 1: | At a temperature of 45 degrees C. and a total exposure time of 90 seconds, the first hexane test resulted in some slight effects. This result is totally unexpected and since it is not noted at higher temperatures it is unlikely to be accurate. Contamination of the solvent is a probable cause and this test will be repeated. |
| Catheters 2–4 | At temperatures of 50, 55 and 60 degrees C. with exposure times of 25 seconds (15 without nitrogen and 10 with nitrogen flowing through the catheter) no effects were noted discrediting the result of catheter 1. |
| Conclusion: | The first test shows the hexane to be effective but that result is highly suspect, especially giving that direct contact with liquid hexane is known to not have any effect on this material other than to swell and soften it. The first test should be repeated. |
| Solvent 4: | Ethyl acetate. |
| Catheter 1: | After a 90 second exposure duration at 55 degrees C. no visible effects were noted. |
| Catheters 2–4: | Raising the time to 60, 65 and 70 degrees C. resulted in a successive loss of stiffness from these catheters while in the vapor atmosphere but no improvement in planarity effects or rounding of the tip was noted. |
| Conclusion: | Ethyl acetate is unlikely to be effective as a one component or multiple component solvent for this process. |
| Solvent 5: | Methyl ethyl ketone (MEK). |
| Catheter 1: | A 90 second exposure time at 60 degrees C. resulted in some reduction in sharp features along cut edges of the catheter. This test was conduct with the same 62 seconds without nitrogen flow through the catheter and 28 seconds with. |
| Catheters 2–4: | After 25 second exposures to 65, 70, and 75 degree C. temperature solvent the only notable additional effect was the flaring to the catheter tip region, an undesirable effect. |
| Conclusion: | Methyl ethyl ketone will not be acceptable as a one component solvent. |
| Solvent 6: | Tetrahydrofuran (THW). |
| Catheter 1: | At 60 degrees C. and 25 seconds of exposure not visible effects are noted, however as that time is extended to 90 seconds some improvements are noted in planarity as indicated by a glossier surface. |
| Catheters 2–4: | Test run at 63, 65 and 67 degrees C. for 25 seconds show continuing improvements but insufficient rounding to consider for use for implanted catheters. |
| Conclusion: | Early testing of tetrahydrofuran in combination with dioxane had shown vexy positive results. This data shows less than expected activity from the one component use of tetrahydrofuran which indicates that it is important to consider the use of other solvents in multiple component solvent mixtures also. The THF may also benefit from higher temperatures but at 67 degrees the solvent begins to boil. The current apparatus design does not allow for the containment of the vapors preventing higher temperature testing of THF. When mixed with a suitable higher boiling point solvent, the boiling point of the mixture is raised allowing the THF to be used at a higher temperature. |
| Solvent 7: | Isopropyl alcohol. |
| Catheter 1: | A 25 second exposure to isopropyl alcohol vapors at 70 degrees C. had no effect on the catheter but continuing the exposure time to 90 seconds did result in small effects in rounding the tip. |
| Catheter 2: | A similar 25 second exposure to 75 degree C. vapors resulted in a slight bending of the tip region but no other effects identified. |
| Catheter 3: | At 80 degrees C. the tip begins to show some rounding effect and a glossy appearance is present in patches over the surface of the catheter. |

| | -continued |
|---|---|
| Catheter 4: | When the boiling point of the alcohol is nearly reached at 82 degrees C. a 25 second exposure provides a nicely rounded tip and a generally glossy surface overall. |
| Conclusion: | Because the boiling point was reached when the first acceptable results were generated, these tests are considered incomplete. While these early results are acceptable the quality of the treated surface did not appear as good as with the dioxane/THF combination. A change to the apparatus or the use of an other solvent to raise the boiling point could allow the isopropyl alcohol to give very good results. This would be a great benefit as isopropyl alcohol is considered far safer than other organic solvents tested here. |
| Solvent 8: | Dioxane. |
| Catheter 1: | Treating the catheter for 25 second in 80 degree C. dioxane give a nicely rounded tip and a glossy appearance to the catheter. |
| Catheters 2 and 3: | At 85 and 90 degrees after 20 seconds and 5 seconds respectively the catheters were destroyed. |
| Conclusion: | Dioxane is a very effective solvent for this process but high temperature used to bring about a sufficient vapor concentration and high activation at those temperatures indicate the need to use it in concert with a lower boiling temperature solvent to give a good latitude for temperature and time of treatment. |
| Solvent 9: | Toluene. |
| Catheter 1: | A 25 second exposure at 100 degrees C. begins to affect the catheter while extending that exposure time to 80 second destroys the catheter. A 45 second exposure still is not enough to eliminate the ridges left by cutting the catheter to length. |
| Catheter 2: | When the temperature is raised to 105 degrees C. the catheter is destroyed after only 17 seconds. |
| Catheters 3 and 4: | At the higher temperatures of 110 and 120 degrees C. the catheter is destroyed almost immediately. |
| Conclusion: | Toluene can not be used as a single component solvent for this process. The temperatures at which the solvent is sufficiently active is approaching the temperature where the catheter material it self can become damaged from the heat. |
| Solvent 10: | Dimethylacetimide: |
| Catheter 1: | At 115 degrees C. the dimethylacetimide yielded one of the best catheters of all solvents tested during a 25 second exposure. Lengthening the exposure time to 45 seconds continued to show a good quality catheter but after 60 second the tip had begun to close in. The catheter was became to limp to flush nitrogen through after 90 seconds. |
| Catheters 2–4: | At temperatures of 120, 125 and 130 degrees C. various forms of catheter deformation became apparent. Additionally, the apparatus was too hot to manipulate between test and excessive quantities may have flashed off leaving insufficient vapors remaining to thoroughly treat the catheter surface. |
| Conclusion: | Dimethylacetimide offers excellent possibilities for this treatment method. Disadvantages include the toxic nature of the chemical and the very high processing temperatures required. |
| Solvent 11: | T. F. Freon |
| Catheter 1–4: | All tests performed at room temperature with no change in the appearance of the catheter after exposure of up to 2 minutes. As can be seen with this data, the polar solvents work on smoothing out the surface of the catheter, while the non-polar solvents are ineffective. Even with the best polar solvents, the temperatures must be reasonably controlled to avoid structural damage to the thin walled catheters. Temperature alone can melt and distort the catheters, so the presence of vapors of solvents at high temperatures can be even more aggressive in damaging the catheters. It is also desirable to minimize condensation on the catheter, especially to the degree where condensation causes rivulets or streams of solvent to run across the surface of the catheter. Such activity is capable of etching or distorting the surface, as occurs to some extent with dipping, and/or can cause dissolved material to redeposit on the surface when the solvent evaporates, leaving detritus on the surface. Condensation can be reduced by heating the catheter, either before or during the solvent treatment so that a condensation surface at lower temperature is not provided. |

The apparatus used in the practice of the preferred embodiment of the invention is a conventional double jacket beaker with a fluid inlet port and a fluid outlet port through which heated fluid is passed to elevate the temperature of a solvent (e.g., the polar solvent) in the bottom of the beaker so that the solvent will enter the vapor phase to treat the medical device placed within the beaker.

What is claimed:

1. A catheter, stent or shunt having a polymeric wall which is about 0.076 mm or less in thickness, manufactured by a process comprising providing a vapor phase comprising a polar solvent, and exposing said polymeric wall component to said vapor phase.

2. A medical device comprising a catheter, stent or shunt for insertion into an animal body, said device comprising at least one element having a wall of extruded polyurethane having the same chemical composition throughout the thickness of said wall which is about 0.076 mm or less in thickness, said wall of extruded polyurethane displaying no thrombogenic effect when inserted into an animal body in contact with blood for a period of at least twenty-four hours after treatment with the process comprising the steps of introducing a medical device that has a polyurethane component into a vapor phase comprising a polar solvent for said polyurethane component, and exposing said polyurethane component on said medical device to said polar solvent without causing a chemical reaction with the polyurethane component.

3. A medical device for insertion into an animal body, said device comprising at least one element having a polymeric wall and a coating of polyurethane, said coating of polyurethane having the same chemical composition throughout the thickness of said coating which is about 0.076 mm or less in thickness, said wall of polyurethane displaying an antithrombogenic effect when inserted into an animal body in contact with blood for a period of at least twenty-four hours, the coating having been treated by a process comprising the steps of introducing the medical device that has a polyurethane coating into a vapor phase comprising a polar solvent for said polyurethane coating, and exposing said polyurethane coating on said medical device to said polar solvent without causing a chemical reaction with the polyurethane coating.

4. The catheter, stent or shunt of claim 1 wherein said polymeric wall has a surface with a topography and exposing said polymeric wall to said vapor phase increases planarity in said topography.

5. The catheter, stent or shunt of claim 1 wherein said polar solvent is at least as polar as toluene.

6. The catheter, stent or shunt of claim 1 wherein said vapor phase comprises a solvent consisting essentially of two different solvents.

7. The catheter, stent or shunt of claim 1 wherein said vapor phase comprises a solvent consisting of two different organic solvents.

8. The catheter, stent or shunt of claim 1 wherein said vapor phase is at a temperature above 40° C.

9. The catheter, stent or shunt of claim 1 wherein said vapor phase comprises tetrahydrofuran and dioxane.

10. The catheter, stent or shunt of claim 1 wherein said catheter is an infusion catheter.

11. The catheter, stent or shunt of claim 1 wherein said catheter has an outside dimension of 1.5 mm or less and a wall thickness of about 0.076 mm or less.

12. The catheter, stein or shunt of claim 1 wherein said catheter has an outside dimension of 1.0 mm or less and a wall thickness of about 0.076 mm or less.

13. The catheter, stein or shunt of claim 1 wherein said catheter has an outside dimension of 0.5 mm or less and a wall thickness of about 0.05 mm or less.

14. The catheter, stent or shunt of claim 1 wherein said catheter has an outside dimension of 1.0 mm or less and wherein the outer surface of the catheter has on average no more than one topographic wave event per 100 square micrometers with the distance from the maximum height of peaks to the maximum depth of an adjacent valley of more than 0.1 micrometers.

15. The catheter, stent or shunt of claim 1 wherein said catheter has an outside dimension of 1.0 mm or less and wherein the outer surface of the catheter has on average no more than one topographic wave event per 100 square micrometers with the distance from the maximum height of peaks to the maximum depth of an adjacent valley of more than 0.05 micrometers.

16. The catheter, stent or shunt of claim 1 wherein an external surface of said polymeric wall has no more than one amplitude event per 100 square micrometer of 0.3 micrometers or greater.

17. The catheter, stent or shunt of claim 1 wherein an external surface of said polymeric wall has no more than one amplitude event per 100 square micrometer of 0.1 micrometers or greater.

18. The catheter, stent or shunt of claim 1 wherein an external surface of said polymeric wall has no more than one amplitude event per 100 square micrometer of 0.05 micrometers or greater.

* * * * *

UNITED STATES PATENT AND TRADEMARK OFFICE
CERTIFICATE OF CORRECTION

PATENT NO.    : 6,774,157 B2
DATED         : August 10, 2004
INVENTOR(S)   : Gregory J. DelMain It is certified that error appears in the above-identified patent and that said Letters Patent is hereby corrected as shown below:

Column 18,
Lines 17 and 20, delete "stein" and insert -- stent --, therefor.

Signed and Sealed this

Fourteenth Day of December, 2004

JON W. DUDAS
*Director of the United States Patent and Trademark Office*